United States Patent
Hsiao

(10) Patent No.: US 11,213,600 B2
(45) Date of Patent: Jan. 4, 2022

(54) ELECTRICAL PLUG TYPE FRAGRANCE LIQUID HEATING AND DIFFUSING DEVICE

(71) Applicant: DONGGUAN YIH TEH ELECTRIC PRODUCTS CO., LTD., DongGuan (CN)

(72) Inventor: Ming Jen Hsiao, Miaoli County (TW)

(73) Assignee: DONGGUAN YIH TEH ELECTRIC PRODUCTS CO., LTD., Dongguan (CN)

(*) Notice: Subject to any disclaimer, the term of this patent is extended or adjusted under 35 U.S.C. 154(b) by 0 days.

(21) Appl. No.: 16/691,866

(22) Filed: Nov. 22, 2019

(65) Prior Publication Data

US 2020/0114034 A1  Apr. 16, 2020

Related U.S. Application Data

(63) Continuation-in-part of application No. 16/162,374, filed on Oct. 16, 2018, now abandoned.

(51) Int. Cl.
*A61L 9/03* (2006.01)

(52) U.S. Cl.
CPC ......... *A61L 9/037* (2013.01); *A61L 2209/133* (2013.01)

(58) Field of Classification Search
CPC ........ A61L 9/14; B05B 7/2443; B05B 7/2459
See application file for complete search history.

(56) References Cited

U.S. PATENT DOCUMENTS

| | | | |
|---|---|---|---|
| 5,192,009 A | 3/1993 | Hidebrands | |
| 5,711,674 A | 1/1998 | Chu | |
| 9,511,166 B1 | 12/2016 | Li | |
| 9,539,355 B2 | 1/2017 | Hsiao | |
| 9,849,206 B1 | 12/2017 | Hsiao | |
| 2007/0207066 A1 | 9/2007 | Thur | |
| 2010/0084484 A1* | 4/2010 | Sevy | A61M 21/00 239/4 |
| 2014/0037273 A1* | 2/2014 | Jaworski | A61L 9/037 392/390 |
| 2014/0133131 A1 | 5/2014 | Hsiao | |
| 2014/0339337 A1 | 11/2014 | Hsiao | |
| 2018/0103507 A1* | 4/2018 | Davis | A61L 9/032 |

* cited by examiner

*Primary Examiner* — Sean E Conley
*Assistant Examiner* — Brendan A Hensel
(74) *Attorney, Agent, or Firm* — Chun-Ming Shih; HDLS IPR Services

(57) ABSTRACT

An electric plug type fragrance liquid heating and diffusing device includes an aroma bottle with a carrier having capillary pores for absorbing an aroma liquid, and a heater for heating the aroma liquid in the capillary pores of the carrier to dissipate the aromatic molecules into the outside air. When the aroma liquid is used up, the aroma bottle can be easily and rapidly detached for replacement. The aroma liquid absorbed by the carrier will not flow out of the carrier even if the aroma bottle is tilted or dumped during use or movement, ensuring safe use.

10 Claims, 5 Drawing Sheets

ELECTRICAL PLUG TYPE FRAGRANCE LIQUID HEATING AND DIFFUSING DEVICE

This application is a Continuation-in-Part of application Ser. No. 16/162,374, filed Oct. 16, 2018.

BACKGROUND OF THE INVENTION

1. Field of the Invention

The present invention relates to scent releasing devices and more specifically, to an electric plug type fragrance liquid heating and diffusing device

2. Description of the Related Art

Aroma diffusers have some problems of heating the aromatic fluid. For example, conventional aroma diffusers use an aroma bottle filled with an aroma liquid for dissipating aroma molecules. The aroma bottle is a glass bottle with an externally threaded bottleneck. In installation, the user needs to thread the externally threaded bottleneck of the aroma bottle upwardly into the inner thread at the bottom side of the aroma diffuser by one single hand. The user often has the disadvantage of not being able to thread the externally threaded bottleneck of the aroma bottle into the inner thread of the aroma diffuser accurately. So, the process of replacing the aroma bottle is slow and inconvenient. Furthermore, the structure of the inner thread of the aroma diffuser is made of a plastic material. The structure of the inner thread of the aroma diffuser will wear quickly with use. If the structure of the inner thread of the aroma diffuser starts to wear, the aroma bottle will loosen up.

The aromas for aroma diffuser are mainly indoor fragrances that contain fragrance oils used in indoor spaces. Generally, the commercially available fragrance oils are not pure ingredients, and they all have certain essential oil carriers. Therefore, the use of these fragrances requires external factors to effectively emit fragrance in indoor spaces. For example, using an aroma heater to heat fragrances for producing good smell, which is different from the use of antiperspirant fragrance or perfume.

SUMMARY OF THE INVENTION

The present invention has been accomplished under the circumstances in view. It is therefore an object of the present invention to provide an electric plug type fragrance liquid heating and diffusing device, which facilitates quick replacement of the aroma bottle when the aroma liquid is used up.

It is therefore another object of the present invention to provide an electric plug type fragrance liquid heating and diffusing device, which has a carrier with capillary pores mounted in the aroma bottle for absorbing the aroma liquid in the bottle body of the aroma bottle so that the aroma liquid absorbed by the carrier will not flow out of the carrier even if the aroma bottle is tilted or dumped during use or movement, ensuring safe use.

To achieve these and other objects of the present invention, an electric plug type fragrance liquid heating and diffusing device comprises a housing, a heater, an electric plug and a bottle holder. The housing is a hollow shell, comprising an opening, a first hole and a second hole. The opening is located on one lateral side of the housing. The second hole is located on the other lateral side of the housing opposite to the opening. The first hole is disposed perpendicularly between the opening and the second hole. The heater is mounted inside the housing. The electric plug is mounted in the first hole and electrically connected with the heater. The bottle holder is mounted in the second hole, comprising a plug hole defined therein and at least one guide groove respectively recessed from the periphery of the plug hole. The electric plug is used to connect to a power supply unit for providing electricity to the heater for generating heat. The heater can be a resistor, a thermistor, a cement resistor or a PTC (Positive Temperature Coefficient) supplemental heater.

The electric plug type fragrance liquid heating and diffusing device further comprises an aroma bottle. The aroma bottle comprises a bottle body, a carrier, a neck, a bottle opening, at least one locating block and an aroma liquid. The aroma liquid is filled in the bottle body. The neck is upwardly extended from an upper side of the bottle body. The bottle opening is formed in a top side of the neck. The locating blocks are respectively extended from the periphery of the neck. The carrier has one side thereof mounted in the bottle opening and disposed in contact with the aroma liquid, and an opposite side thereof extended out of the bottle opening. The internal capillary pores of the carrier absorb the aroma liquid. The aroma liquid is continuously absorbed by the capillary pores of the carrier and transferred to the part of the carrier outside the bottle opening. The aroma liquid residing inside the capillary pores of the carrier can contact the air to volatilize the aroma molecules. The aroma liquid does not flow over the carrier, so the electric plug type fragrance liquid heating and diffusing device is safer to use the aroma bottle. However, some fragrance liquids, such as scented essential oil carriers, do not readily release aroma molecules at room temperature and require heating to release aroma molecules.

DETAILED DESCRIPTION OF THE PREFERRED EMBODIMENT

Figure 1:
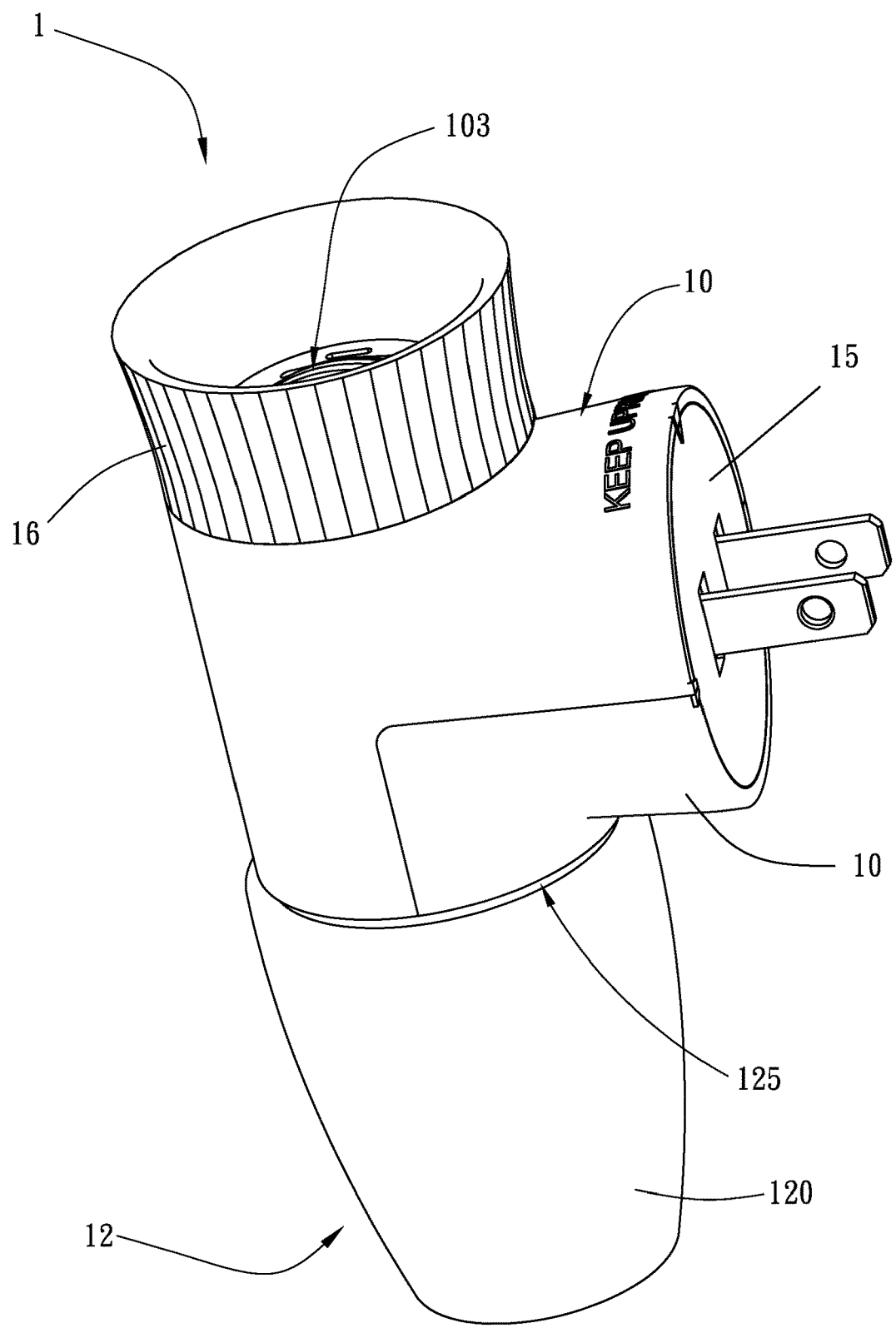
FIG. 1 is an oblique top elevation of an electrical plug type fragrance liquid heating and diffusing device in accordance with the present invention.
Figure 2:
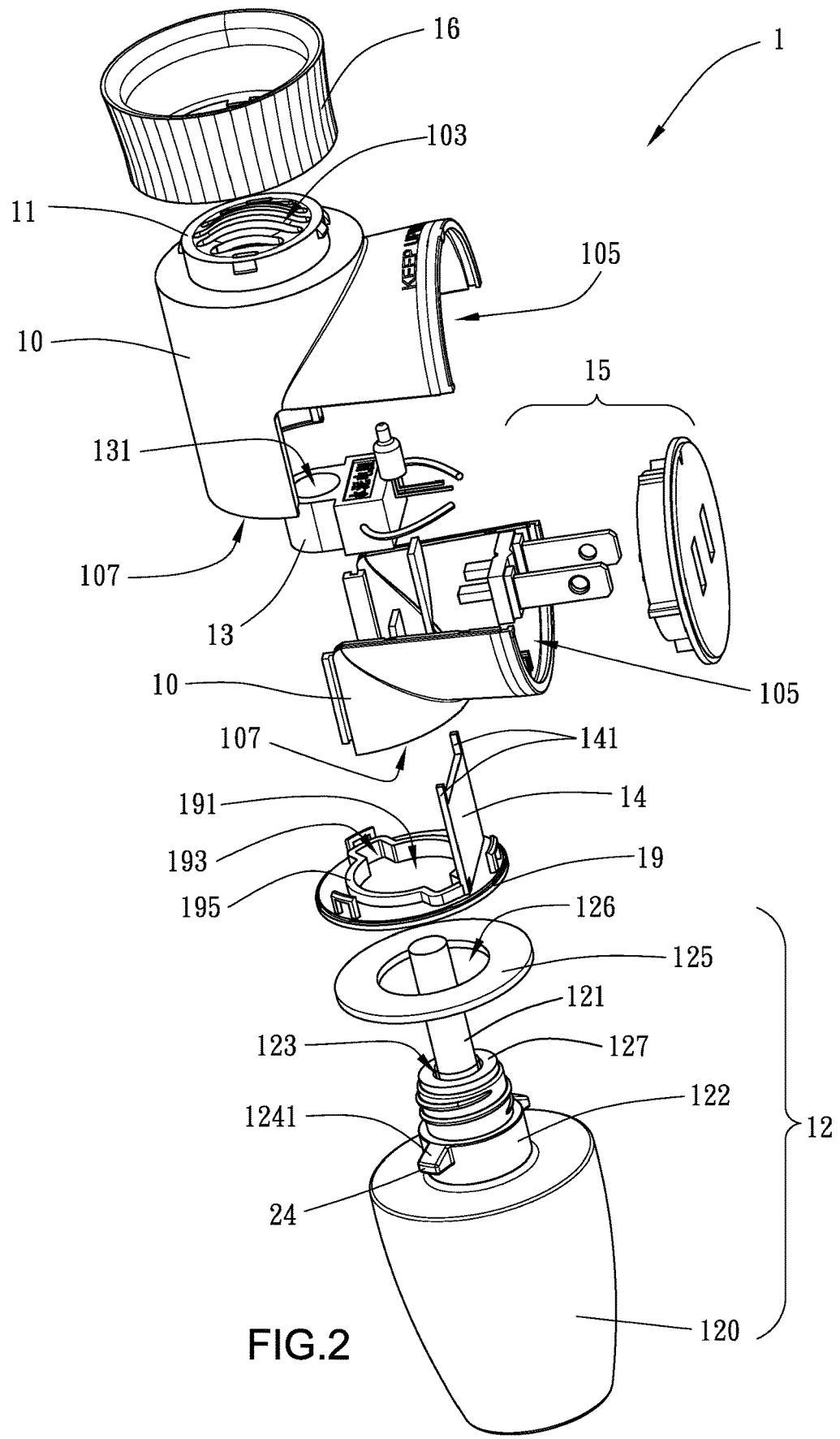
FIG. 2 is an exploded view of the electrical plug type fragrance liquid heating and diffusing device in accordance with the present invention.
Figure 3:
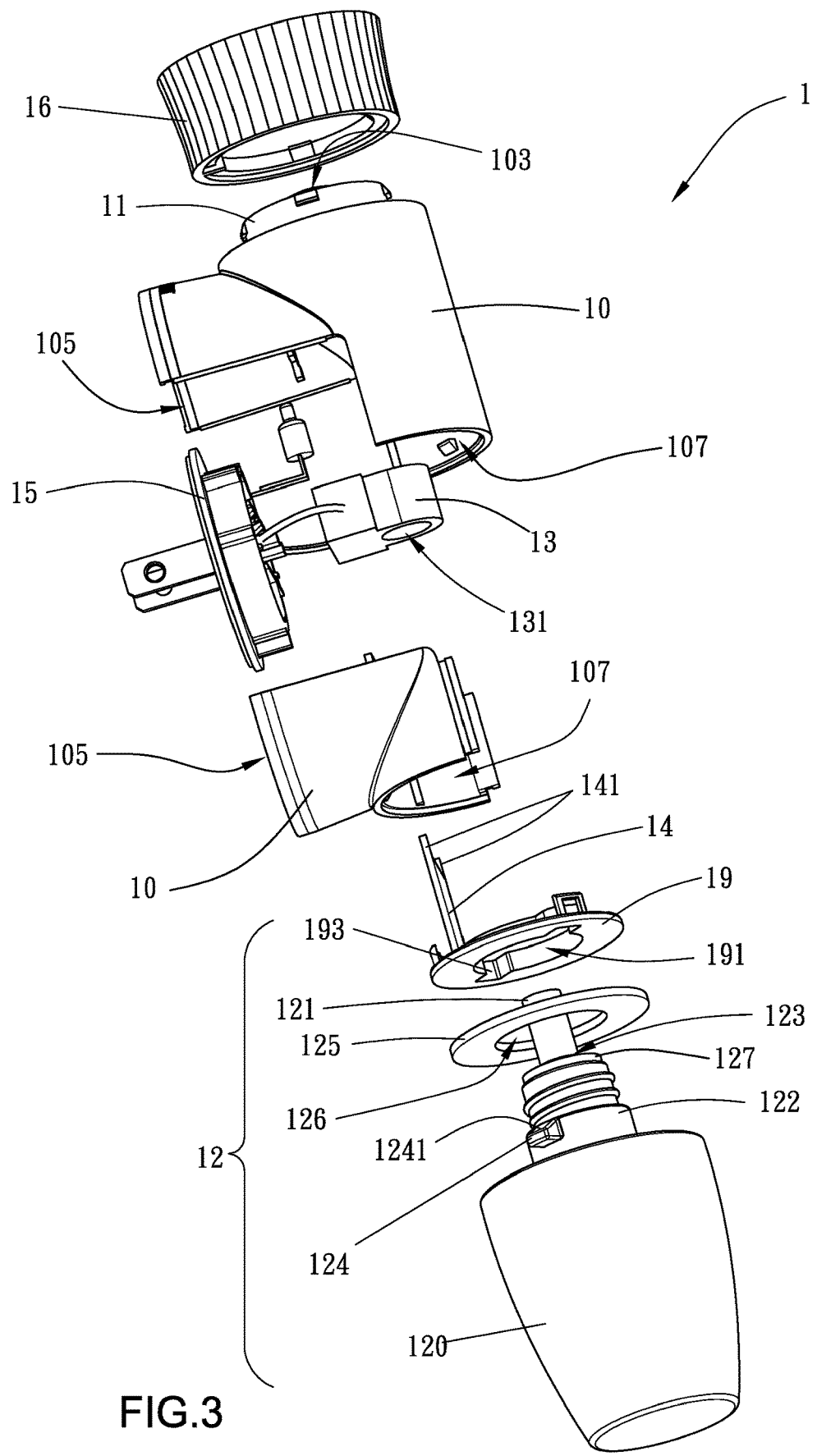
FIG. 3 corresponds to FIG. 2 when viewed from another angle.
Figure 4:
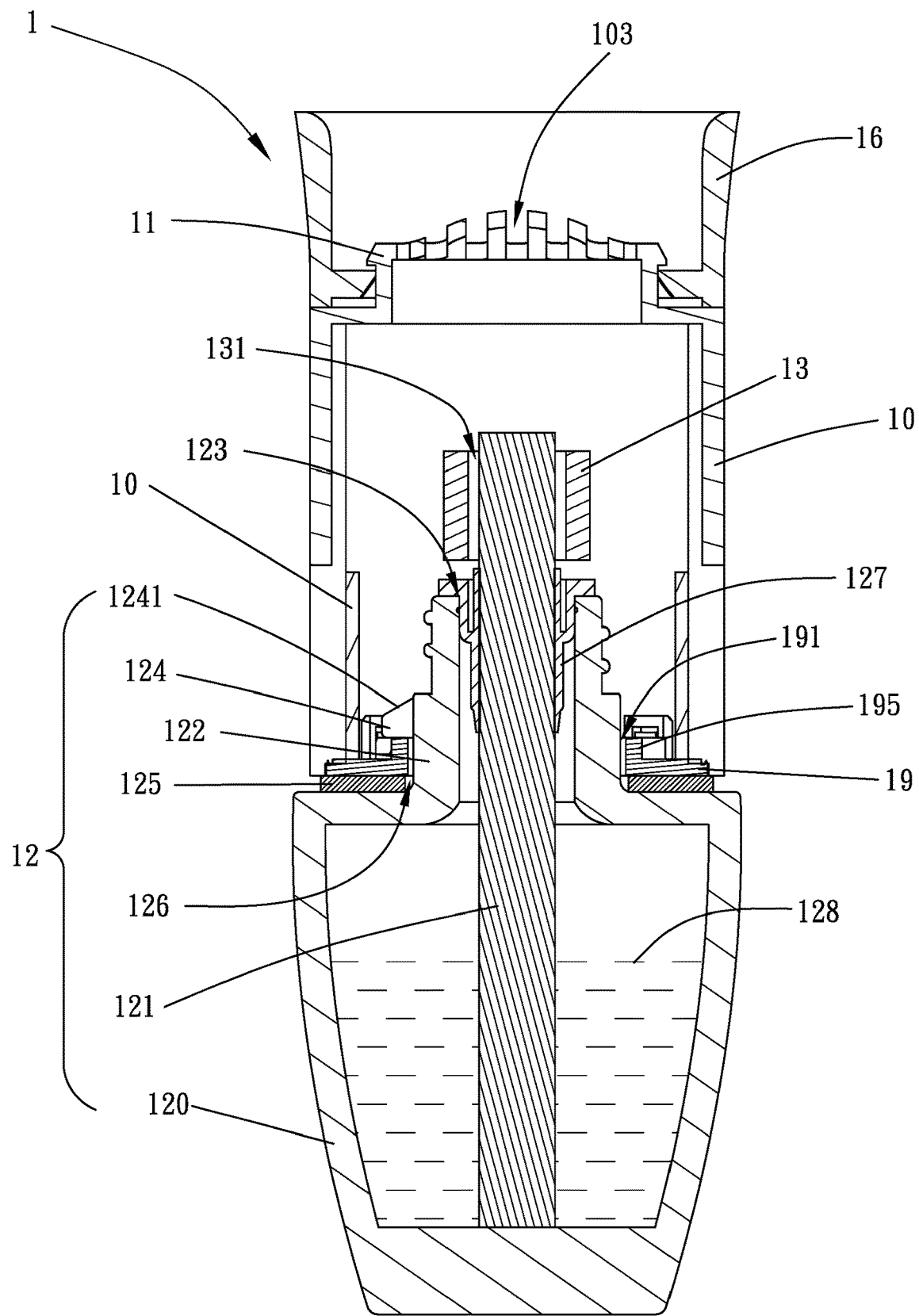
FIG. 4 is a sectional side view of the electrical plug type fragrance liquid heating and diffusing device in accordance with the present invention.
Figure 5:
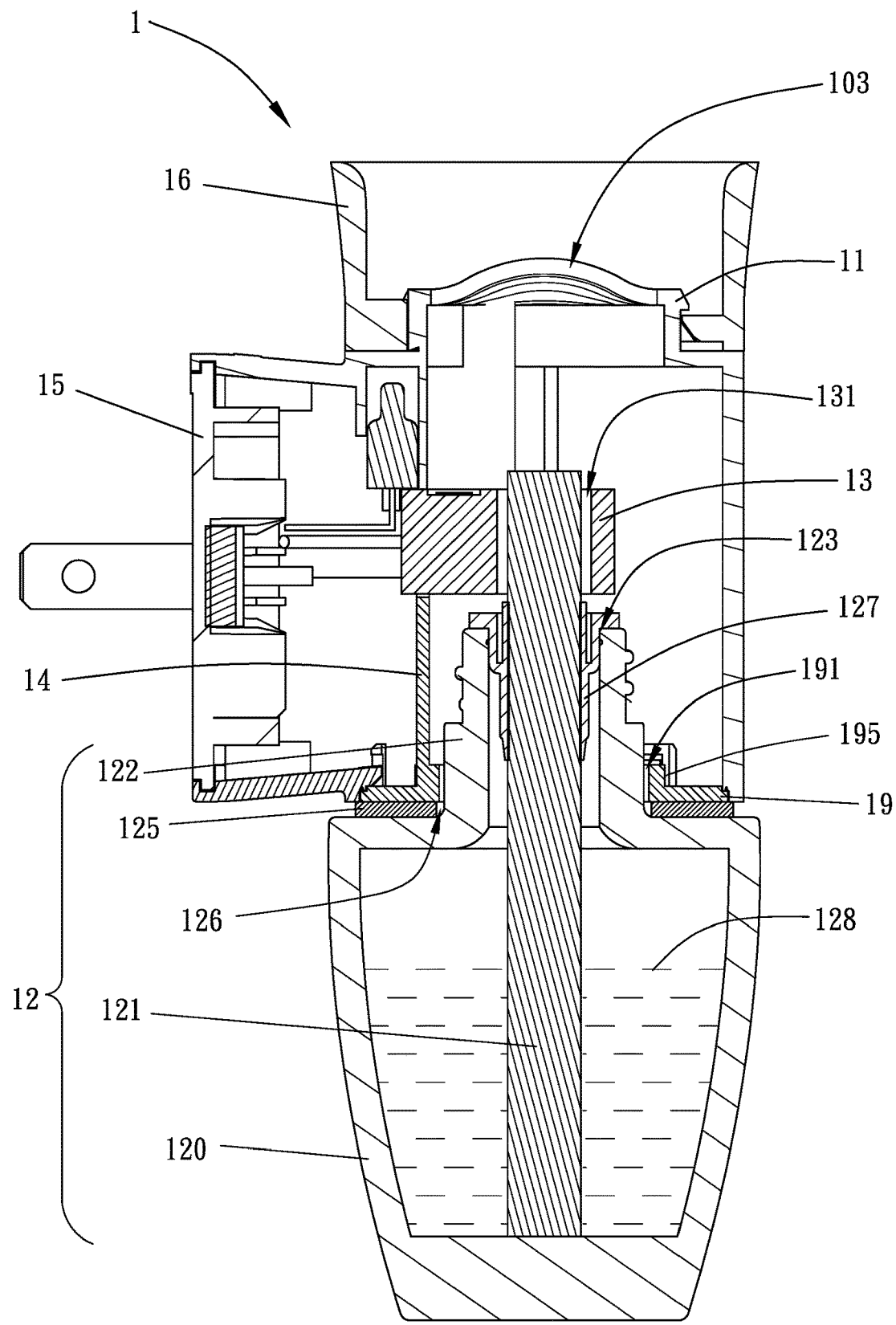
FIG. 5 is a sectional front view of the electrical plug type fragrance liquid heating and diffusing device in accordance with the present invention.

Referring to FIGS. 1-5, an electric plug type fragrance liquid heating and diffusing device 1 in accordance with the present invention is shown. The electric plug type fragrance liquid heating and diffusing device 1 comprises a back cover 10, a thermal conduction unit 11, a heater 13, an electrical plug 15, a front cover 17, and a bottle holder 19.

electric plug type fragrance liquid heating and diffusing device 1 comprises a housing 10, a heater 13, an electric plug 15, and a bottle holder 19. The housing 10 is a hollow shell. The housing 10 has an opening 103, a first hole 105 and a second hole 107. The opening 103 is located on one lateral side of the housing 10. The second hole 107 is located on the other lateral side of the housing 10 opposite to the opening 103. The first hole 105 is perpendicularly disposed between the opening 103 and the second hole 107. The heater 13 is mounted inside the housing 10. The electric plug 15 is coupled to the first hole 105. The heater 13 is electrically connected to the electric plug 15. The bottle holder 19 is coupled to the second hole 107. The bottle holder 19 has a plug hole 191, and at least one guide groove 193 located in the plug hole 191. The plug hole 191 is opened inside the bottle holder 19. The guide groove 193 is recessed from the side of the plug hole 191. In the present preferred embodiment, as illustrated in the annexed drawings, two guide grooves 193 are provided. The electric plug 15 is used to connect to a power supply unit (not shown) to provide power to the heater 13 for generating heat. The heater 13 is, for example, a resistor, a thermistor, a cement resistor or a PTC (Positive Temperature Coefficient) supplemental heater.

Referring to FIGS. 2-5 again, the electric plug type fragrance liquid heating and diffusing device 1 further comprises an aroma bottle 12. The aroma bottle 12 comprises a bottle body 120, a carrier 121, a neck 122, a bottle opening 123, at least one locating block 124, and an aroma liquid 128. The aroma liquid 128 is filled in the bottle body 120. The neck 122 extends from the upper side of the bottle body 120. The bottle opening 123 is formed at the upper end of the neck 122. The locating block 124 is formed on either side of the surface of the neck 122. The carrier 121 has one side thereof joined to the aroma liquid 128 in the bottle opening 123, and an opposite side thereof extended out of the bottle opening 123. The carrier 121 has capillary pores to absorb the aroma liquid 128. The aroma liquid 128 is continuously absorbed by the capillary of the carrier 121 and transported to the carrier 121 outside the bottle opening 123. The aroma liquid 128, which resides inside the capillary pores of the carrier 121, can contact the air to quickly and efficiently dissipate the aroma molecules. The aroma liquid 128 does not flow over the carrier 121, so the electric plug type fragrance liquid heating and diffusing device is safer to use the aroma bottle. However, some fragrance liquids, such as scented essential oil carriers, do not readily release aroma molecules at room temperature and require heating to release aroma molecules.

Referring to FIGS. 1-5 again, the at least one locating block 124 symmetrically matches the number of the at least one guide groove 193. The at least one guide groove 193 or the at least one locating block 124 may be one or more. In the present preferred embodiment, the number of the at least one guide groove 193 and the number of the at least one locating block 124 are symmetrically two.

The aroma bottle 12 provided with the carrier 121 of the present invention can be quickly and detachably engaged in the bottle holder 19. The neck 122 and carrier 121 of the aroma bottle 12 are inserted through the plug hole 191. After the locating blocks 124 passed through the respective guide grooves 193, the aroma bottle 12 is rotated relative to the bottle holder 19 by an angle to either the left or the right side, so that the aroma bottle 12 can be engaged in the bottle holder 19 above the plug hole 191. The side of the carrier 121 that extends out of the bottle opening 123 is disposed adjacent to the heater 13. The electric plug 15 is connected to a power source and electrically connected to the heater 13. The power source supplies power to the heater 13 to generate a heat source. The heat source is transferred to the carrier 121 and conducted to the aroma liquid 128 in the carrier 121. As the temperature increases, the aroma liquid 128 agglomerates the movement of the aromatic molecules, and the collision probability between the molecules becomes larger, resulting in more effective collisions, and the reaction is faster, thereby effectively volatilizing the aroma liquid 128 into fine aromatic molecules from the capillary of the carrier 121, and thus, the volatilized aromatic molecules are dissipated outward to the environment and mixed with air to produce aroma. In contrast, the locating blocks 124 of the aroma bottle 12 can be rotated to the upper side of the respective guide grooves 193 and moved downwardly through the respective guide grooves 193, enabling the aroma bottle 12 to be separated from the plug hole 191.

In some embodiments, the bottle opening 123 of the aroma bottle 12 is internally engaged with a stopper 127. The stopper 127 is engaged inside the bottle opening 123. The carrier 121 has the outer side thereof passes through the stopper 127. The stopper 127 is used to further fix the carrier 121 at the bottle opening 123, and further prevent the aroma liquid 128 from leaking from the bottle opening 123. Preferably, the stopper 127 is made of an elastic material such as rubber, plastic or silicone rubber.

In the preferred embodiment of the present invention, the aperture of the guide grooves 193 is larger than the volume of the locating blocks 124. While the neck 122 of the aroma bottle 12 is placed in the plug hole 191, the user can attach the locating blocks 124 to the bottom surface of the bottle holder 19 and then rotate the aroma bottle 12 to move the locating blocks 124 to the lower side of the respective guide grooves 193. At this moment, the fingers of the user can sense the tactile sensation of the locating blocks 124 touching the respective guide grooves 193, or the user even can hear the auditory sound of the locating blocks 124 colliding with the depressed guide grooves 193. At this time, the user only needs to gently push the aroma bottle 12 upwards so that the locating blocks 124 can easily fall upward into the respective guide grooves 193 and pass the respective guide grooves 193. Thereafter, the user can use the fingers to rotate the aroma bottle 12 relative to the bottle holder 19 by an angle to either the left or the right side, so that the aroma bottle 12 can be engaged in the bottle holder 19 above the plug hole 191. In contrast, the locating blocks 124 of the aroma bottle 12 can be rotated by an angle to the left or right side to the upper side of the respective guide grooves 193. At this moment, the fingers of the user can sense the tactile sensation of the locating blocks 124 touching the respective guide grooves 193, or the user even can hear the auditory sound of the locating blocks 124 colliding with the depressed guide grooves 193. At this time, the user only needs to gently push the aroma bottle 12 downwards so that the locating blocks 124 can easily fall downward into the respective guide grooves 193 and pass the respective guide grooves 193, and thus, the aroma bottle 12 is disengaged from the plug hole 191 of the bottle holder 19. The design of the electric plug type fragrance liquid heating and diffusing device 1 facilitates mounting the aroma bottle 12 in the plug hole 191 or replacing the aroma bottle 12. Compared with the threaded mount type aroma bottles of the conventional aroma diffuser designs, the invention is convenient and rapid to use, and the aroma bottle 12 can be stably assembled in the plug hole 191 without loosening.

Referring to FIGS. 2-4 again, the bottle holder 19 further comprises a locating flange 195 upwardly extended from the periphery of the plug hole 191 and the guide grooves 193 to a predetermined height. The width of the upper edge of the locating flange 195 may be less than the length of the locating blocks 124. The depth of the inner side of the plug hole 191 and the guide grooves 193 is increased. Thus, when the user pushes the locating blocks 124 of the aroma bottle 12 into the respective guide grooves 193, the sense of touch is more clearer and smoother. Furthermore, the length of the locating blocks 124 is greater than the width of the upper edge of the locating flange 195, and the locating blocks 124 can be smoothly moved along the upper edge of the locating flange 195, facilitating smooth use of the aroma bottle 12 in the electric plug type fragrance liquid heating and diffusing device 1.

Referring to FIGS. 2-4 again, in the preferred embodiment of the present invention, the upper side of the locating block 124 is formed with a slope 1241 which is gradually raised from the free end of the locating block 124 toward the neck 122, so that the locating block 124 can be pushed up into the respective guide groove 193 more smoothly.

Referring to FIGS. 2-5 again, the aroma bottle 12 further comprises a seat cushion 125, and a third hole 126 is formed in the center of the seat cushion 125. The seat cushion 125 has an elastic function. The seat cushion 125 can be made of materials such as silicone, plastic, sponge or cloth. By means of the third hole 126, the seat cushion 125 can be attached onto the neck 122 at the bottom side of locating blocks 124. When mounting the aroma bottle 12 in the plug hole 191 of the bottle holder 19, the seat cushion 125 is attached between the bottom side of the neck 122 and the bottle holder 19. The locating blocks 124 can be rotationally fixed on the upper side of the plug hole 191, and the elasticity and elastic adjustment function provided by the seat cushion 125 allow the aroma bottle 12 to engage with the bottle holder 19 more closely.

Referring to FIGS. 2-5 again, the electric plug type fragrance liquid heating and diffusing device 1 further comprises a bracket 14. The bracket 14 comprises a plurality of bracket components 141 respectively extended from two opposite sides thereof. The bracket components 141 at one side of the bracket 14 are fastened to the bottle holder 19. The bracket components 141 at the opposite side of the bracket 14 are fastened to the heater 13. Thus, the bracket 14 holds the heater 13 steadily inside the housing 10, keeping the heater 13 in proximity to the upper side of the carrier 121.

Referring to FIGS. 2-5 again, the heater 13 has a heat collection structure 131. The heat collection structure 131 may be formed by opening a hole in the middle of the heater 13. Alternatively, the heat collection structure 131 can be a curved wall extending around the border area of the heater 13. Thus, the inner space of the hole or the curved wall forms a heat collection area. The carrier 121 has at least a part thereof surrounded by the heat collection structure 131 so that the generated heat source can be used to uniformly heat the carrier 121, improving the heating effect of the aroma liquid 128 in the carrier 121. Preferably, the heat collection structure 131 shown in the annexed drawings is a cylindrical hole. In the present preferred embodiment, the upper side of the carrier 121 suspends in the cylindrical hole of the heat collection structure 131 so that the aroma liquid 128 in the carrier 121 can be efficiently heated to dissipate aromatic molecules.

Referring to FIGS. 1-5 again, the housing 10 further comprises an annular flange 11 and a guide cup 16. The annular flange 11 extends from the border edge of the opening 103 to a height. The guide cup 16 is a tubular shell coupled to the outer wall of the annular flange 11 and disposed in communication with the space inside the annular flange 11. The heat source generated by the heater 1 heats the aroma liquid 128 in the capillary pores of the carrier 121 to dissipate aromatic molecules that pass through the space inside the annular flange 11 and are guided by the guide cup 16 upwardly into the outside air.

In some embodiments of the present invention, the carrier 121 can be any of a variety of absorbers that can absorb the aroma liquid 128, store the aroma liquid 128 and prevent the aroma liquid 128 from flowing. The carrier 121 can be heated to transfer the heated temperature to the aroma liquid 128 in the capillary pores thereof, causing the aroma liquid 128 to be volatilized and diffused through the air. The carrier 121 can be a fiber bundle, a porous plastic material, such as porous PE plastic product, a porous ceramic, a porous gypsum product, or a suction core (cotton, foam, cloth).

Although a particular embodiment of the present invention has been described in detail for purposes of illustration, various modifications and enhancements may be made without departing from the spirit and scope of the invention. Accordingly, the invention is not to be limited except as by the appended claims.

What the invention claimed is:

1. An electric plug fragrance liquid heating and diffusing device, comprising:
    a housing with an opening, a first hole and a second hole, said opening being located on one lateral side of said housing, said second hole being located on an opposite lateral side of said housing, said first hole being perpendicularly disposed between said opening and said second hole;
    a heater mounted inside said housing;
    an electric plug mounted in said first hole of said housing and electrically connected with said heater;
    a bottle holder mounted in said second hole, said bottle holder comprising a plug hole defined therein and at least one guide groove recessed from the periphery of said plug hole;
    an aroma bottle, wherein a top surface of a bottle body of the aroma bottle comprises a shoulder area and a neck integrally formed with the bottle body and extending upwardly; and
    a seat cushion disposed on the shoulder area, wherein the seat cushion is made of elastic material;
    wherein an upper part of the neck is a threaded portion, and at least one locating block protrudes from a periphery of the neck below the threaded portion;
    wherein the neck passes through the seat cushion and the bottle holder, and
    wherein a top surface and a bottom surface of the seat cushion are in direct contact with the bottle holder and the shoulder area, respectively.

2. The electric plug fragrance liquid heating and diffusing device as claimed in claim 1, wherein said bottle holder further comprises a locating flange upwardly extended from the border of said plug hole and the border of each said guide groove.

3. The electric plug fragrance liquid heating and diffusing device as claimed in claim 2, wherein said aroma bottle further comprises a carrier, a bottle opening, and an aroma liquid, said aroma liquid being filled in said bottle body, said neck being upwardly extended from an upper side of said bottle body, said bottle opening being formed in a top side of said neck, said carrier having one side thereof mounted in said bottle opening and disposed in contact with said aroma liquid and an opposite side thereof extended out of said bottle opening.

4. The electric plug fragrance liquid heating and diffusing device as claimed in claim 3, wherein quantities of said at least one guide groove and said at least one locating block are 2, respectively.

5. The electric plug fragrance liquid heating and diffusing device as claimed in claim 3, wherein each said locating block has a slope formed on a top side thereof, said slope extending upwardly from a free end of the associating said locating block toward said neck.

6. The electric plug fragrance liquid heating and diffusing device as claimed in claim 3, wherein each said locating flange has an upper edge with a width less than the length of each said locating block.

7. The electric plug fragrance liquid heating and diffusing device as claimed in claim 3, wherein said seat cushion has a third hole formed in the center thereof and coupled to said neck beneath said at least one locating block.

8. The electric plug fragrance liquid heating and diffusing device as claimed in claim 1, further comprising a bracket, said bracket comprising a plurality of bracket components respectively extended from two opposite sides thereof, the said bracket components at one side of said bracket being fastened to said bottle holder, the said bracket components at the opposite side of said bracket being fastened to said heater.

9. The electric plug fragrance liquid heating and diffusing device as claimed in claim 3, wherein said heater further comprises a heat collection structure selectively formed of a hole in a middle part of said heater or a curved wall extended along one side of said heater with a heat collection area defined therein; said carrier has at least a part thereof surrounded by said heat collection structure.

10. The electric plug fragrance liquid heating and diffusing device as claimed in claim 1, wherein said housing further comprises an annular flange extended from the border of said opening to a predetermined height, and a guide cup made in the form of a tube and fastened to the periphery of said annular flange.

* * * * *